United States Patent [19]

Sakuma et al.

[11] Patent Number: 5,584,688
[45] Date of Patent: Dec. 17, 1996

[54] MEDICINE INJECTION DEVICE

[75] Inventors: Shuji Sakuma; Kiminori Atsumi, both of Tokyo, Japan

[73] Assignee: Sangi Co., Ltd., Tokyo, Japan

[21] Appl. No.: 274,241

[22] Filed: Jul. 13, 1994

[30] Foreign Application Priority Data

Mar. 22, 1994 [JP] Japan ................................. 6-075284
Apr. 27, 1994 [JP] Japan ................................. 6-113716

[51] Int. Cl.⁶ .................................................. A61C 5/02
[52] U.S. Cl. ............................ 433/81; 433/175; 433/215; 433/229; 604/891.1
[58] Field of Search ................................. 433/215, 224, 433/229, 219, 173, 174, 175, 176, 81, 218; 604/77, 93, 891.1

[56] References Cited

U.S. PATENT DOCUMENTS

| | | | |
|---|---|---|---|
| 4,412,825 | 11/1983 | Tokarz | 433/229 |
| 4,523,910 | 6/1985 | Makovich | 433/215 |
| 4,671,768 | 6/1987 | Ton | 433/80 |
| 4,959,052 | 9/1990 | Cox | 604/891.1 |
| 5,090,903 | 2/1992 | Taylor | 433/229 |

FOREIGN PATENT DOCUMENTS

| | | | |
|---|---|---|---|
| 2247736 | 9/1972 | Germany | 433/229 |
| 1669445 | 8/1991 | U.S.S.R. | 433/215 |
| 1729503 | 4/1992 | U.S.S.R. | 433/173 |

*Primary Examiner*—Cary E. O'Connor
*Attorney, Agent, or Firm*—Steinberg, Raskin & Davidson, P.C.

[57] ABSTRACT

A medicine injection device capable of continuously administrating a medicine to the body of a patient over a long period of time while keeping the patient from being restrained during administration. The medicine injection device includes a medicine container and at least one medicine passage each arranged in at least one of a root and a crown, so that a medicine stored in the medicine container is administrated through the medicine passage to the body of a patient.

17 Claims, 5 Drawing Sheets

MEDICINE INJECTION DEVICE

BACKGROUND OF THE INVENTION

This invention relates to an injector for injecting a medicine into the body, and more particularly a medicine injection device for gradually and continuously injecting a medicine into the body.

Conventionally, gradual injection of a medicine such as a tonic, insulin, an anticancer drug or the like into the body over a long period of time has been carried out through an improvement in preparations such as capsulation of the medicine, compression of the medicine by means of a filler or the like. Alternatively, it has been accomplished using a self-sustaining injector such as an injector equipped with a cylinder pump or the like.

Unfortunately, the above-described remedies which have been conventionally employed for continuous injection of the medicine meet with difficulties. More particularly, the former remedy renders embedding of the medicine in place in the body of a patient difficult. Also, preparation of the medicine is hard to be controlled depending on the medicine, resulting in an effect of the medicine being often varied with time.

The latter remedy requires to set the self-sustaining injector outside the body of a patient. Unfortunately, this significantly bears a load on the patient irrespective of a size of the injector. Also, this causes the patient to constantly pay attention to breakage of the injector or accidental or unexpected removal thereof from the body during injection of the medicine, resulting in a further load being borne on the patient, so that the patient's life in society is often subject to substantial restriction.

Further, injection of the medicine through the injector causes a damage to the body of a patient, particularly, the vein.

Thus, it is highly desirable to develop a medicine injection device which is capable of preventing a patient from being restrained during injection of a medicine and readily accomplishing daily administration of a medicine without bearing a burden on the patent for a long period of time, to thereby provide the patient with a continuous effect of the medicine.

SUMMARY OF THE INVENTION

Accordingly, it is an object of the present invention to provide a medicine injection device for injecting a medicine into the body of a patient which is capable of keeping the patient from being restrained during injection or administration of the medicine.

It is another object of the present invention to provide a medicine injection device which is capable of readily accomplishing daily injection or administration of a medicine into a patient to provide the patient with a continuous effect of the medicine.

It is a further object of the present invention to provide a medicine injection device which is capable of effectively keeping a patient from being subjecting to restriction on a daily life and a life in society.

It is still another object of the present invention to provide a medicine injection device which is capable of controlling a rate of injection or administration of a medicine to the body as desired.

In accordance with the present invention, a medicine injection device is provided. The medicine injection device includes a medicine container arranged so as to straddle at least one of an artificial root and an artificial crown and adapted to store a medicine therein. The artificial root is formed with at least one medicine passage for permitting the medicine in the medicine container to be introduced into the body therethrough.

In a preferred embodiment of the present invention, the medicine container constitutes the artificial root.

Also, in accordance with the present invention, a medicine injection device is provided. The medicine injection device includes a medicine container and at least one medicine passage formed in a natural root.

In a preferred embodiment of the present invention, the medicine passage comprises a tube arranged in a root canal of the root.

In a preferred embodiment of the present invention, the medicine container constitutes an artificial crown.

In a preferred embodiment of the present invention, the medicine container is made of a material exhibiting rubber elasticity.

In a preferred embodiment of the present invention, the medicine container is fixed at the root and covered with the artificial crown.

In a preferred embodiment of the present invention, the medicine container is provided with a micro pump.

BRIEF DESCRIPTION OF THE DRAWINGS

These and other object and many of the attendant advantages of the present invention will be readily appreciated as the same becomes better understood by reference to the following detailed description when considered in connection with the accompanying drawings in which like reference numerals designate like or corresponding parts throughout; wherein.

DETAILED DESCRIPTION OF THE PREFERRED EMBODIMENTS

Now, a medicine injection device according to the present invention will be described hereinafter with reference to the accompanying drawings.

Figure 1:
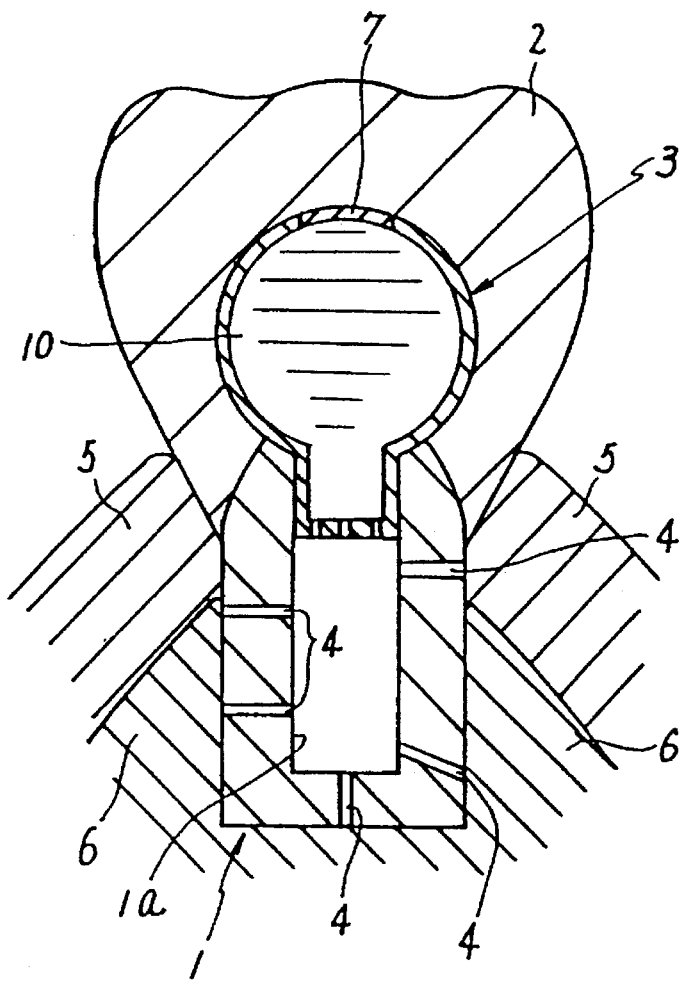
FIG. 1 is a sectional view showing a first embodiment of a medicine injection device according to the present invention.
Figure 2:
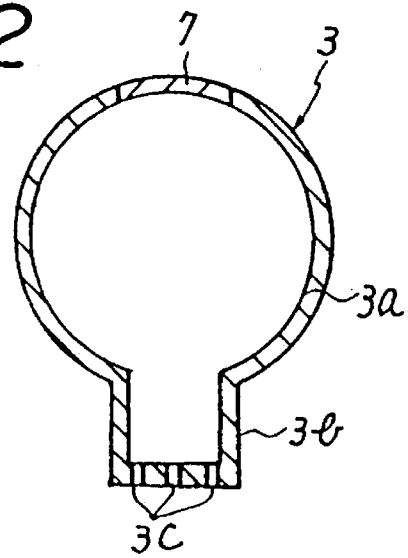
FIG. 2 is a sectional view showing an essential part of the medicine injection device of FIG. 1.

Referring first to FIGS. 1 and 2, a first embodiment of a medicine injection device according to the present invention is illustrated. A medicine injection device of the illustrated embodiment includes an artificial root 1 embedded in an alveolar bone 6 of a patient or a human being. The artificial root 1 is formed therein with a cavity section 1a. Also, the artificial root 1 is formed with at least one medicine passage 4 for permitting a gingiva 5 and the cavity section 1a to communicate with each other therethrough. In the illustrated embodiment, a plurality of such medicine passages 4 are formed through the artificial root 1. The cavity section 1a has a medicine container 3 to be received therein. The medicine container 3 is generally formed into a keyhole-like shape as shown in FIGS. 1 and 2 and includes a hollow container section 3a of a substantially circular shape in section and a hollow insertion section 3b formed into a rectangular shape in section and communicating with the container section 3a as shown in FIG. 2. The insertion section 3b is formed into a configuration which permits the insertion section 3b to be snugly fitted in the cavity section 1a of the artificial root 1. The insertion section 3b is formed at a bottom thereof with a plurality of through-holes 3c. The container section 3b is formed into a volume which permits a medicine 10 to be stored in a sufficient amount in the container section 3b. The container section 3a is provided at a top thereof with a lid 7 in an openable or removable manner, so that it may be rendered open or removed from the container section 3a to permit the medicine 10 to be introduced into the container section 3a when replenishment of the medicine 10 is required.

Reference numeral 2 designates an artificial crown which is put on the artificial root 1 so as to cover it, so that the medicine container 3 may be fully covered with the artificial crown 2 and surround by the artificial root 1 and crown 2.

The artificial root 1 and artificial crown 2 may be constructed in substantially the same manner as those conventionally prepared for an artificial tooth in a dental office.

Now, the manner of operation of the medicine injection device of the illustrated embodiment constructed as described above will be described hereinafter.

First, the artificial root 1 is embedded in a portion of the alveolar bone 6 from which a tooth is drawn. At this time, arrangement of the artificial root 1 is carried out in such a manner that a part of the medicine passages 4 is positioned on a side of the gingiva 5 and the remaining part of the passages 4 is positioned on a side of the alveolar bone 6.

After the artificial root 1 is thus embedded in the alveolar bone 6, the insertion section 3b of the medicine container 3 in which the medicine 10 is previously stored is fitted in the cavity section 1a of the artificial root 1. The medicine 10 to be previously stored in container section 3a is selected depending on a treatment intended. Following setting of the medicine container 3 in the artificial root 1, the artificial crown 2 is put on the artificial root 1, to thereby cover the medicine container 3.

Thus, the medicine 10 stored in the medicine container 3 is permitted to flow via the through-holes 3c into the cavity 1a of the artificial root 1 and then ooze from the cavity 1a through the medicine passages 4 to the gingiva 5 and alveolar bone 6. In particular, when the medicine 10 in the medicine container 3 is expanded by a bodily temperature of a patient or by expansion of air in the container 3 due to the bodily temperature, oozing of the medicine 10 from the container 3 is promoted.

The medicine injection device of the illustrated embodiment is adapted to control a rate of injection or administration of the medicine 10 per unit time. More particularly, the rate of administration of the medicine 10 may be controlled by determining the number and size of the through-holes 3c of the insertion section 3b of the medicine container 3 and the number and size of the medicine passages 4 depending on a treatment aimed.

The illustrated embodiment, as described above, is so constructed that the medicine passages 4 are formed so as to communicate with the gingiva 5 and alveolar bone 6. Alternatively, the medicine passages 4 may be formed so as to communicate with any one of the gingiva 5 and alveolar bone 6.

When administration of the medicine 10 to the body carried out as described above causes the medicine container 3 to be emptied of the medicine 10, the artificial crown 2 is removed from the artificial root 1, followed by removal or opening of the lid 7, resulting in replenishment of the medicine 10.

Setting of the medicine injection device of the illustrated embodiment in the body in the manner described above permits administration of the medicine to the body to be continued until the medicine container 3 is emptied of the medicine 10. Thus, the medicine injection device readily accomplishes daily injection of the medicine into the body of a patient to provide the patient with a continuous effect of the medicine. Also, the medicine container 3 is fully covered with the artificial crown 2, so that the medicine injection device effectively keeps the patient from being subjecting to restriction on a daily life and a life in society.

In the illustrated embodiment, as described above, the medicine container 3 independently or separately formed is embedded in the body in a manner to straddle the artificial root 1 and artificial crown 2. Alternatively, the artificial root and artificial crown 2 may be formed with a cavity common to both or separate cavities communicating with each other, so that the cavity or cavities may act as the medicine container. Thus, it will be noted that in the present invention, the medicine container involves, for example, a cavity commonly formed in the artificial root 1 and artificial crown 2 so as to straddle both, cavities respectively formed therein so as to communicate with each other, and the like.

When the medicine container 3 is directly formed in the artificial root and artificial crown, a rate of administration of the medicine is controlled by the number and size of the medicine passages 4 formed at the artificial root 1.

Figure 3:
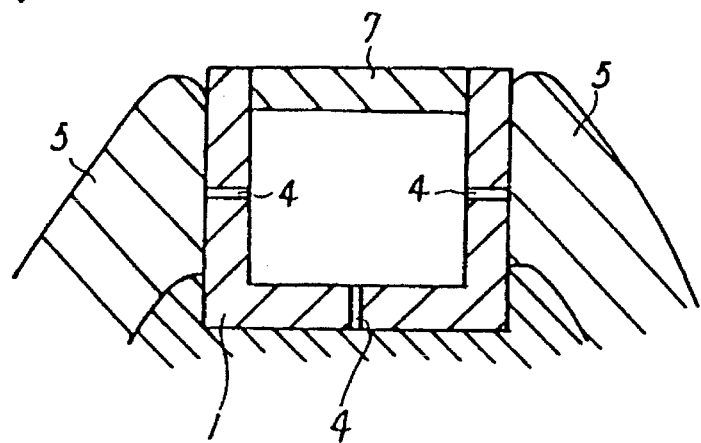
FIG. 3 is a sectional view showing a second embodiment of a medicine injection device according to the present invention.

Referring now to FIG. 3, a second embodiment of a medicine injection device according to the present invention is illustrated. A medicine injection device of the second embodiment includes only an artificial root 1 of a hollow rectangular shape, which per se acts as a medicine container 3 in which a medicine is stored. The artificial root 1 is formed with medicine passages 4 and provided on a top thereof with a lid 7. The remaining part of the medicine injection device of the second embodiment may be constructed in substantially the same manner as the first embodiment described above. Thus, the second embodiment may exhibit not only the same function and advantage as the first embodiment described above but an additional advantage of reducing the number of parts and simplifying a structure thereof. As will be noted from the above, the medicine injection device of the second embodiment is free of an artificial crown. However, it may include an artificial crown arranged so as to cover the artificial root 1. The number and size of the medicine passages 4 formed at the artificial root 1 may be determined depending on a rate of administration of the medicine.

Figure 4:
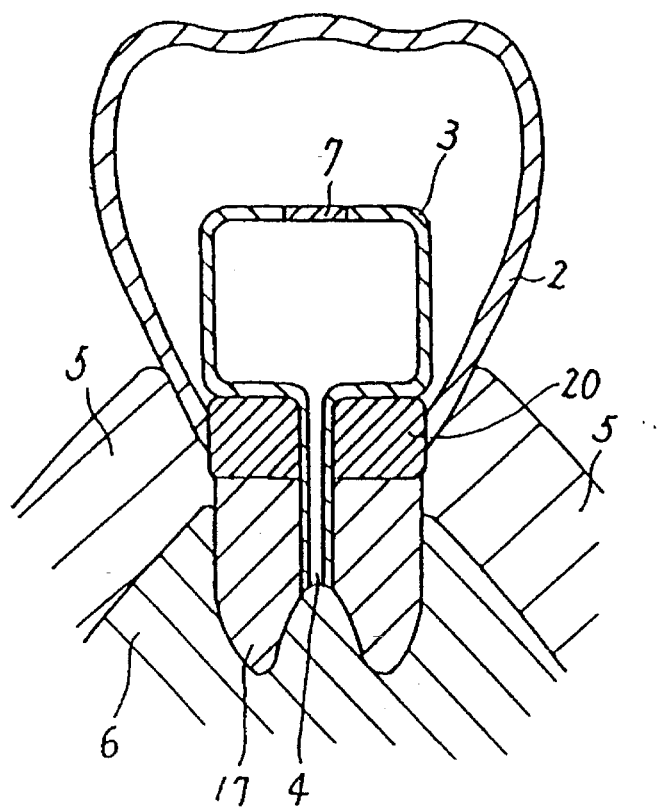
FIG. 4 is a sectional view showing a third embodiment of a medicine injection device according to the present invention.

Referring now to FIG. 4, a third embodiment of a medicine injection device according to the present invention is illustrated. A medicine injection device of the third embodiment includes an artificial root of a substantially rectangular and hollow shape acting as an medicine container 3. The medicine container 3 is formed with at least one medicine passage 4. The artificial root or medicine container 3 is supported on a dental support 20 made of a suitable material such as a dental cement material or the like and arranged between the artificial root or medicine container 3 and a natural root 17 of a patient. The medicine passage 4 is formed so as to extend through the dental support 20 and natural root 17. The medicine container 3 thus formed and arranged is covered with an artificial crown 2.

In the medicine injection device of the third embodiment constructed as described above, a medicine (not shown) stored in the medicine container 3 is gradually injected through the medicine passage 4 into the body of a patient. When the container 3 is emptied of the medicine, the artificial crown 2 is removed from the container 3, followed by removal of the lid 7, resulting in replenishment of the medicine to the medicine container 3 being carried out.

Figure 5:
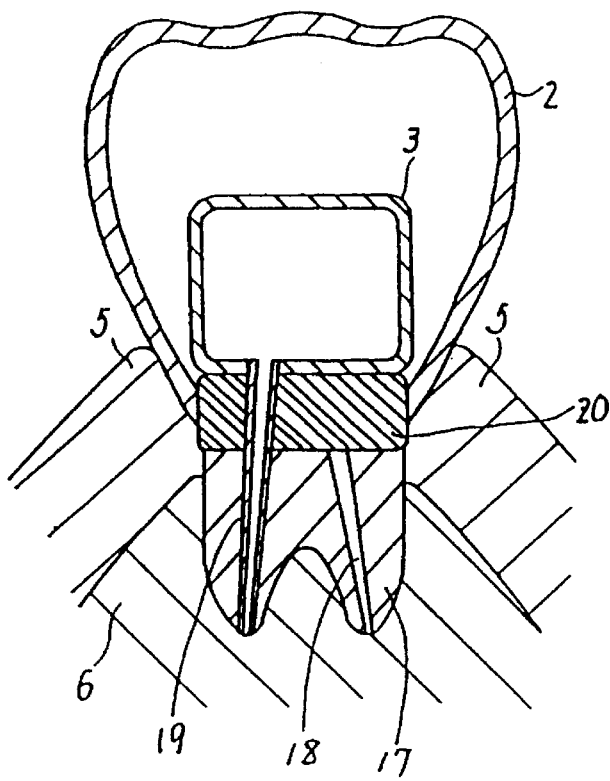
FIG. 5 is a sectional view showing a fourth embodiment of a medicine injection device according to the present invention.

Referring now to FIG. 5, a fourth embodiment of a medicine injection device according to the present invention is illustrated. A medicine injection device of the fourth embodiment includes a medicine container 3 which is free of any lid like the lid 7 in each of the above-described embodiments and at least one medicine passage comprising a tube 19 such as a tube post conventionally used for a dental treatment. The tube post 19 is releasably connected to the medicine container 3 through an opening formed at the container 3 and is arranged in a root canal of a natural root 17 of a patient from which nerves are removed. The remaining part of the fourth embodiment may be constructed in substantially the same manner as the third embodiment described above.

In the fourth embodiment constructed as described above, a medicine (not shown) in the medicine container 3 is injected through the tube post 19 into the body of a patient. When the medicine container 3 is emptied of the medicine, it is removed from the tube post 19, followed by replenishment of a medicine to the medicine container 3 through the opening of the container.

In the third and fourth embodiments described above, it is not necessarily required that the medicine passage is arranged so as to pass through the natural root 17. It is merely required that the medicine passage 4 communicates with any communication passage such as a hole or a gap formed in the natural root 17 and communicating with the body of a patient. However, it will be noted that formation of the medicine passage 4 by means of the tube post 19 arranged through the root canal 18 from which nerves are removed advantageously eliminates a necessity of forming such a communication passage as described above.

As will be noted from the above, the artificial crown 2 is not necessarily required in the medicine injection device of the present invention. However, when the medicine container 3 is arranged so as to act also as the artificial crown 4, a patient is ensured to freely bite foods through the artificial crown 4.

Figure 6:
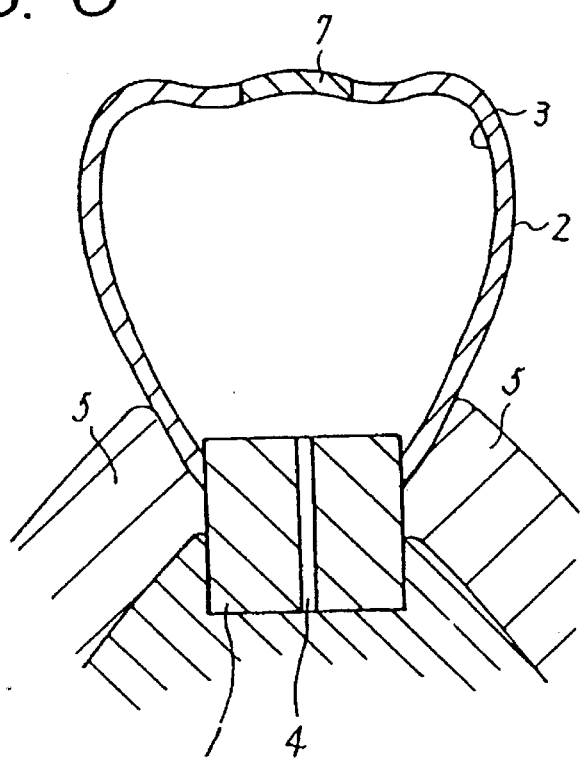
FIG. 6 is a sectional view showing a fifth embodiment of a medicine injection device according to the present invention.

Referring now to FIG. 6, a fifth embodiment of a medicine injection device according to the present invention is illustrated. A medicine injection device of the fifth embodiment is so constructed that only an artificial crown 2 is formed into a hollow configuration so as to act as a medicine container 3 and provided at a top thereof with a lid 7 in a releasable manner. Thus, the artificial crown 2 serves also as the medicine container 3, therefore, the fifth embodiment reduces the number of parts and simplifies a structure thereof. Also, the lid 7 is provided directly at the artificial crown 2, so that replenishment of a medicine to the medicine injection device may be readily carried out without removing the artificial crown 2. An artificial root 1 is formed with at least one through-hole or medicine passage 4. In the fifth embodiment, a rate of administration of the medicine is controlled depending on the number and size of the medicine passages 4 as in the above-described embodiments.

Figure 7:
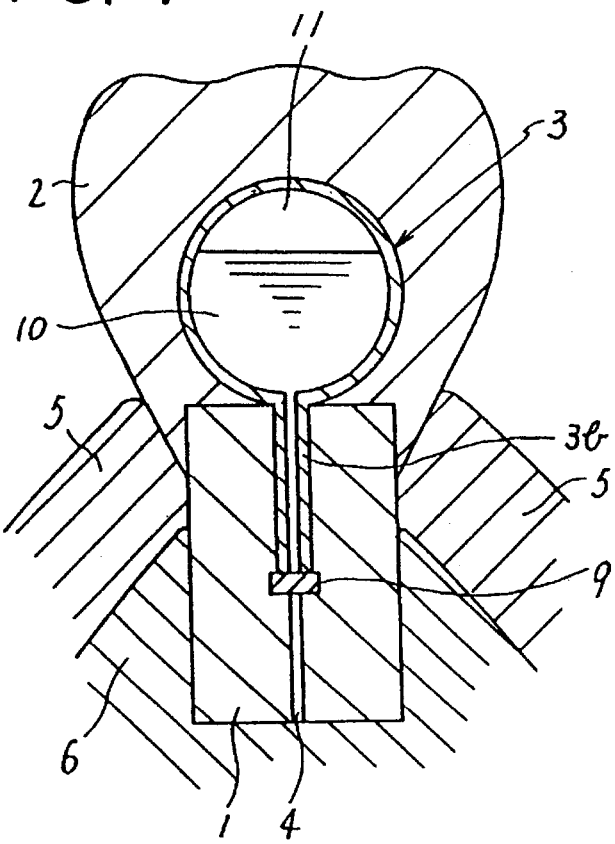
FIG. 7 is a sectional view showing a sixth embodiment of a medicine injection device according to the present invention.

Referring now to FIGS. 7, a sixth embodiment of a medicine injection device according to the present invention is illustrated. A medicine injection device of the sixth embodiment includes an artificial root 1 formed with at least one medicine passage 4 and an artificial crown 2 arranged so as to cover the artificial root 1. In the illustrated embodiment, a medicine container 3 is arranged so as to straddle both the artificial crown 2 and artificial root 1. More particularly, the medicine container 3 includes a container section arranged in the artificial crown 2 and an insertion section 3b arranged in the artificial root 1 and communicating with both the container section and medicine passage 4. The insertion section 3b of the medicine container 3 is provided at a distal end or outlet port thereof with a membrane or film 9.

The medicine container 2 has a medicine 10 and air 11 stored therein. The film 9 is formed so as to permit the medicine 10 to pass therethrough and prevent from blood or the like flowing backward from the body of a patient through the medicine passage 4 to the insertion section 3b. A rate of administration of the medicine 10 to the patient is controlled depending on the number of medicine passages 4 and a size thereof, and a diameter of the insertion section 3b of the medicine container 3. The air 11 received above the medicine 10 in the container section is varied in pressure or volume depending on a temperature in the mouth of a patient, to thereby promote administration of the medicine 10.

Figure 8:
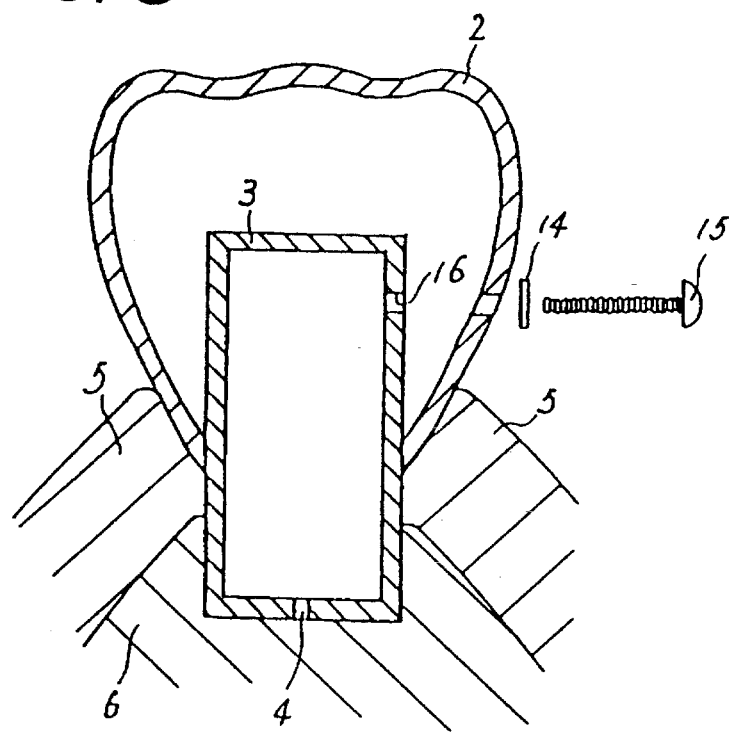
FIG. 8 is a sectional view showing a seventh embodiment of a medicine injection device according to the present invention.

Referring now to FIG. 8, a seventh embodiment of a medicine injection device according to the present invention is illustrated. A medicine injection device of the seventh embodiment is so constructed that an artificial root or medicine container 3 and an artificial crown 2 are closed by a common lid comprising a combination of a washer 14 and a screw 15. For this purpose, the medicine container 3 is formed with a medicine port 16. Thus, when the medicine container 3 is emptied of a medicine, the screw 15 is released from the container 3 and artificial crown 2, resulting in eliminating a necessity of removing the artificial crown 2 from the medicine container 3. When the medicine port 16 is provided away from the artificial crown 2, replenishment of the medicine may be carried out through the medicine port 16 of the medicine container 3 by means of a needle or the like.

In the illustrated embodiment, the lid is provided commonly to the medicine container 3 and artificial crown 2.

However, it is a matter of course that the container 3 and crown 2 may be provided with independent lids, respectively.

As will be noted from the above, the sixth and seventh embodiments each are so constructed that the medicine container is set in a natural root.

Figure 9:
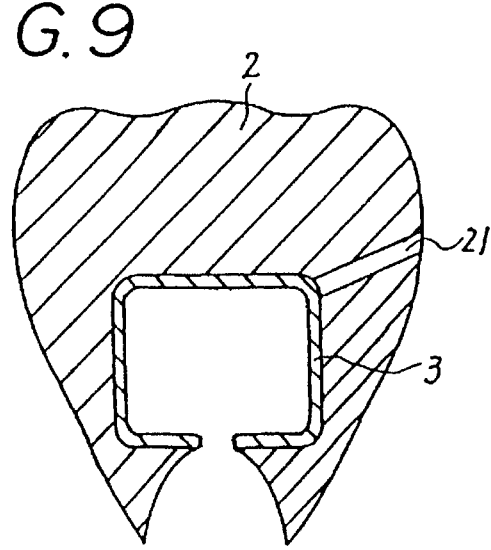
FIG. 9 is a sectional view showing an eighth embodiment of a medicine injection device according to the present invention.

Referring now to FIG. 9, an eighth embodiment of a medicine injection device according to the present invention is illustrated. In a medicine injection device of the eighth embodiment, a medicine container 3 is made of an elastic rubber material and is covered with an artificial crown 2 formed with a passage 21 for replenishment of a medicine to the container 3. Replenishment of the medicine is carried out by inserting a needle or the like into the medicine container 3 made of rubber through the passage 21 of the artificial crown 2. After the replenishment, the needle is drawn out from the container 3. The container is made of elastic rubber, so that a portion of the container pierced by the needle is clogged due to elasticity of the rubber, resulting in eliminating a necessity of providing the container 3 with any lid.

Figure 10:
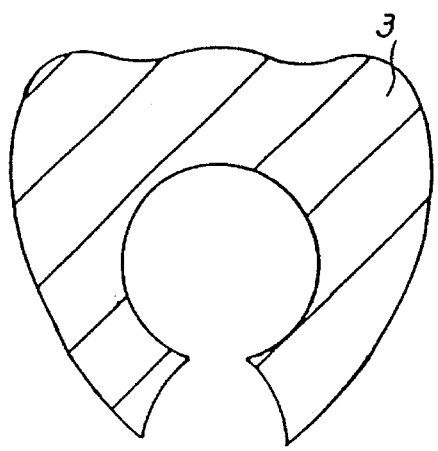
FIG. 10 is a sectional view showing a ninth embodiment of a medicine injection device according to the present invention.

Referring now to FIG. 10, a ninth embodiment of a medicine injection device according to the present invention is illustrated. A medicine injection device of the illustrated embodiment is so constructed that a medicine container 3 is made of a rubber material and acts also as an artificial crown. Replenishment of a medicine is carried out in a manner similar to the eighth embodiment described above with reference to FIG. 9. Also, the illustrated embodiment permits insertion of a needle into the container 3 to be carried out at any desired portion of the container 3 because an artificial crown independent from the medicine container 3 is not provided.

In each of the eighth and ninth embodiments described above, the medicine container 3 is made of a rubber material. However, it may be formed of any other material such as a plastic material or the like so long as the material exhibits rubber elasticity. Also, the medicine container may be likewise applied to an artificial root or a natural root.

Figure 11:
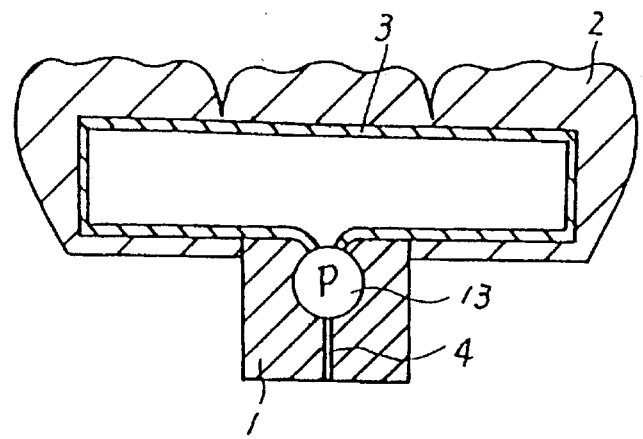
FIG. 11 is a sectional view showing a tenth embodiment of a medicine injection device according to the present invention.

Referring now to FIG. 11, a tenth embodiment of a medicine injection device according to the present invention is illustrated. A medicine injection device of the tenth embodiment includes an artificial root 1 formed with at least one medicine passage 4, a medicine container 3, a micro pump 13 for forcibly feeding a medicine from the medicine container 3 through the medicine passage 4 to the body of a patient, and an artificial crown 2 formed into a configuration and a size corresponding to those of two or more teeth. The medicine container is arranged so as to straddle both the artificial crown 2 and artificial root 1. In the illustrated embodiment, the artificial crown 2, as descried above, is formed into a configuration and a size corresponding to those of a plurality of teeth, so that a space in which the medicine container 3 is to be arranged may be significantly increased, resulting in increasing a volume of the container 3. Therefore, the embodiment permits the medicine to be fed over a significantly increased period of time irrespective of use of the micro pump 13. Also, such an increase in volume of the container decreases the number of times of replenishment of the medicine and permits control of a rate of administration of the medicine by the micro pump 13 to be accomplished at an increased degree of freedom.

In the present invention, the medicine container 3 may be made of any suitable material such as a rigid resin material, a soft resin material or the like so long as it is safe to the human body. The medicine stored in the medicine container 3 may be encapsulated in a capsule made of a gelatin film.

In this instance, the gelatin film is dissolved and then permitted to pass through the medicine passage 4 together with the medicine.

The diameter, number and position of the medicine passage 4 formed in the artificial root or natural root 17 are selected depending on a type of the medicine to be administrated, a rate of administration thereof and the like. The medicine passage 4 may be arranged so as to communicate with the vein. Such arrangement of the passage 4 permits flowing of blood in the body to promote gradual administration of the medicine through the medicine passage 4.

As can be seen from the foregoing, the medicine injection device of the present invention keeps a patient from being restrained during administration of a medicine and ensures continuous administration of the medicine. Therefore, the present invention permits a medicine which is required to be administrated over a long period of time as in a treatment of a chronic disease to be continuously injected into a patient over an increased period of time, to thereby provide a patient with a continuous effect of the medicine. Also, the present invention effectively keeps a patient from being subjecting to restriction on a daily life and a life in society and controls a rate of injection or administration of a medicine as desired.

While preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A medicine injection device for introducing medicine into the body into or at a location under the gingiva, comprising:

an artificial root adapted to extend at least in part into the gingiva and being formed with at least one medicine passage, and a medicine container arranged so as to straddle said artificial root and adapted to store a medicine therein;

said passage permitting the medicine in said medicine container to be introduced into the body therethrough into or at a location under the gingiva.

2. A medicine injection device as defined in claim 1, wherein said medicine container constitutes said artificial root.

3. A medicine injection device as defined in claim 1 wherein said medicine container has the shape of an artificial crown.

4. A medicine injection device as defined in claim 3, wherein said artificial crown is operatively coupled to said artificial root.

5. A medicine injection device as defined in claim 1, wherein said medicine container is made of a material exhibiting rubber elasticity.

6. A medicine injection device as defined in claim 1, further comprising an artificial crown separable from said medicine container for covering said medicine container.

7. A medicine injection device as defined in claim 1, wherein said medicine container is provided with a micro pump.

8. A medicine injection device as defined in claim 1, wherein said medicine container also straddles an artificial crown.

9. A medicine injection device for placement in connection with a natural root of a tooth having at least one passage therein leading into the gingiva and for introducing medicine into the body through the at least one passage in the natural root, comprising:

an artificial crown; and a medicine container arranged in said artificial crown and receivable of a medicine to be administered into the body, said at least one medicine passage adapted to be in flow communication with said medicine container such that the medicine flows from said medicine container through said at least medicine passage in the root into the gingiva.

10. A medicine injection device as defined in claim 9, wherein said medicine passage comprises a tube arranged in a root canal of said root.

11. A medicine injection device as defined in claim 9, wherein said medicine container constitutes said artificial crown.

12. A medicine injection device as defined in claim 9, wherein said medicine container is made of a material exhibiting rubber elasticity.

13. A medicine injection device as defined in claim 9, wherein said medicine container is adapted to be fixed at the root and said artificial crown is separable from and covers said medicine container.

14. A medicine injection device as defined in claim 9, wherein said medicine container is provided with a micro pump.

15. A medicine injection device for introducing medicine into the body through a natural root of a tooth or an artificial root, said root having at least one passage therein leading into the gingiva, comprising:

an artificial crown adapted for placement onto said root, said artificial crown including a medicine container for receiving a medicine, said medicine container adapted to be in flow communication with said at least one medicine passage for permitting the medicine in said medicine container to be introduced into the body said at least one passage, said medicine container being made of a material exhibiting rubber elasticity.

16. A medicine injection device as defined in claim 15, wherein said artificial crown further includes a replenishment passage extending from an exterior of said artificial crown to said medicine container.

17. A medicine injection device, comprising:

an artificial root, an artificial crown operatively coupled to said artificial root, a medicine container arranged so as to straddle at least one of said artificial root and said artificial crown and adapted to store a medicine therein, said artificial root being formed with at least one medicine passage for permitting the medicine in said medicine container to be introduced into the body therethrough, and a pump arranged in connection with said at least one medicine passage to regulate the flow of the medicine through said at least one medicine passage.

* * * * *